United States Patent
Nishikubo

(10) Patent No.: US 9,833,814 B2
(45) Date of Patent: Dec. 5, 2017

(54) COMPOSITE PIEZOELECTRIC BODY, ULTRASOUND PROBE, AND ULTRASOUND DIAGNOSTIC IMAGING APPARATUS

(71) Applicant: KONICA MINOLTA, INC., Chiyoda-ku, Tokyo (JP)

(72) Inventor: Yuichi Nishikubo, Kawasaki (JP)

(73) Assignee: KONICA MINOLTA, INC., Tokyo (JP)

( * ) Notice: Subject to any disclaimer, the term of this patent is extended or adjusted under 35 U.S.C. 154(b) by 924 days.

(21) Appl. No.: 14/194,352

(22) Filed: Feb. 28, 2014

(65) Prior Publication Data
US 2014/0257109 A1    Sep. 11, 2014

(30) Foreign Application Priority Data
Mar. 5, 2013   (JP) ................................ 2013-042468

(51) Int. Cl.
| | |
|---|---|
| *A61B 8/00* | (2006.01) |
| *B06B 1/06* | (2006.01) |
| *H01L 41/37* | (2013.01) |
| *H01L 41/337* | (2013.01) |
| *H01L 41/083* | (2006.01) |
| *H01L 41/27* | (2013.01) |

(52) U.S. Cl.
CPC ............ *B06B 1/067* (2013.01); *A61B 8/4483* (2013.01); *H01L 41/337* (2013.01); *H01L 41/37* (2013.01); *A61B 8/4444* (2013.01); *H01L 41/083* (2013.01); *H01L 41/27* (2013.01); *Y10T 29/42* (2015.01)

(58) Field of Classification Search
CPC ................................................... A61B 8/4444
See application file for complete search history.

(56) References Cited

U.S. PATENT DOCUMENTS

| | | | | |
|---|---|---|---|---|
| 5,295,487 | A  * | 3/1994 | Saitoh ...................... | B06B 1/06 310/334 |
| 5,497,540 | A  * | 3/1996 | Venkataramani ..... | B06B 1/0622 29/25.35 |
| 5,629,906 | A  * | 5/1997 | Sudol .................... | B06B 1/0681 310/326 |
| 2004/0024320 | A1* | 2/2004 | Karasawa ............. | B06B 1/0622 600/459 |
| 2009/0102319 | A1* | 4/2009 | Nakatsuka ............... | H03H 3/02 310/326 |
| 2011/0020585 | A1* | 1/2011 | Steinfeldt ........... | C04B 41/4505 428/70 |

FOREIGN PATENT DOCUMENTS

| | | |
|---|---|---|
| JP | 2004088056 A | 3/2004 |
| JP | 4609902 B2 | 12/2011 |

OTHER PUBLICATIONS

Japanese Office Action (and English translation thereof) dated Feb. 9, 2016, issued in counterpart Japanese Application No. 2013-042468.

\* cited by examiner

*Primary Examiner* — Rajeev Siripurapu
(74) *Attorney, Agent, or Firm* — Holtz, Holtz & Volek PC

(57) ABSTRACT

A method for producing a composite piezoelectric body includes: forming a composite piezoelectric body by filling a non-conductive polymer between a plurality of piezoelectric materials arranged in an array state at predetermined intervals, and polishing one surface of the composite piezoelectric body, from which surface at least the piezoelectric materials and the polymer are exposed, by using an abrasive film in which an abrasive particle is applied to a base film.

5 Claims, 4 Drawing Sheets

COMPOSITE PIEZOELECTRIC BODY, ULTRASOUND PROBE, AND ULTRASOUND DIAGNOSTIC IMAGING APPARATUS

BACKGROUND OF THE INVENTION

Field of the Invention

The present invention relates to a method for producing a composite piezoelectric body, a method for producing an ultrasound probe, a composite piezoelectric body, an ultrasound probe and an ultrasound diagnostic imaging apparatus.

Description of Related Art

Ultrasound generally means sound wave of 16000 Hz or more, and is applied to various fields such as a defect test and a disease diagnosis because it can examine an inside of an object nondestructively, harmlessly, and in approximately real time. As one of them, there is an ultrasound diagnostic imaging apparatus which scans an inside of a test object with ultrasound, and images an internal state of the test object on the basis of a received signal generated from reflective wave of ultrasound propagating from the inside of the test object. This ultrasound diagnostic imaging apparatus is, as for medical use, more compact and more inexpensive than other medical imaging apparatuses, and has various characteristics, for example, high level of safety because of being free from the risk of exposure to radiation such as X-ray. For this reason, the ultrasound diagnostic imaging apparatus is widely used for a circulatory system (for example, coronary arteries of a heart, etc.), digestive system (for example, a stomach and intestines, etc.), internal medicine (for example, a liver, pancreatic, spleen, etc.), urinary system (for example, a kidney, bladder, etc.), obstetric and gynecologic system, and so on.

In the ultrasound diagnostic imaging apparatus, an ultrasound probe for transmitting/receiving ultrasound to/from a test object is used. The ultrasound probe is equipped with a plurality of ultrasound transducers each of which mechanically vibrates on the basis of a transmitting electronic signal to generate ultrasound, by utilizing piezoelectric phenomenon, and receives reflective wave of ultrasound generated due to an acoustic impedance difference in the test object to generate a received electronic signal. The ultrasound probe is constituted by arranging the ultrasound transducers, for example, in one-dimensional array state or two-dimensional array state.

Heretofore, as such piezoelectric element, a single ceramic material such as lead zirconate titanate (PZT) has been adopted. However, in recent years, a composite piezoelectric body in which ceramic materials are placed at regular intervals and polymer such as epoxy resin fills therebetween has come to be used.

In the case of using such composite piezoelectric body as an ultrasound transducer, it is necessary to form an electrode on the surface thereof. However, there is a problem that unevenness occurs on the surface due to the difference of properties of the polymer and the ceramic material in grinding or polishing processing executed in production process, and as a result, the electrode cannot be formed uniformly. Moreover, if the portion of the ceramic material is dented from the surface of the composite piezoelectric body, namely, if the polymer bulges from the surface of the composite piezoelectric body, the polymer is not restrained on its sides, and thereby sometimes thermally expands freely. Even when such expansion is small, the polymer easily expands/contracts due to heat generated in electrode formation by sputtering, vapor deposition, or soldering. Furthermore, when the composite piezoelectric body is adhered to other components, additional pressure is added thereto in order to remove extra adhesive agent. At that time, stress is concentrated in the polymer, and the polymer, which is softer than the ceramic, is pushed inward. Accordingly, the electrode existing in the vicinity of the boundary between the ceramic material and the polymer is damaged, and sometimes disconnecting of the electrode occurs.

In view of such problems, there is disclosed a technique that performs etching to the polymer portion so that it is dented from the ceramic material portion by utilizing the difference between decomposition rates of the ceramic material and the polymer by plasma etching, and suppresses thermal expansion of the polymer by utilizing adhesiveness in boundary portion of sides of the ceramic material and the polymer, for example, in Japanese Patent No. 4609902.

SUMMARY OF THE INVENTION

However, there is a possibility that a polarization structure of a ceramic material becomes disrupted (depolarizes) thermally and electrically in plasma etching processing. In this case, the depolarizing ceramic material needs to be subjected to polarization treatment again. At that time, the composite piezoelectric body does not have sufficient rigidity (stiffness) because it has been substantially ground or polished so as to have a certain thickness, and thereby production difficulty such as deformation of the composite piezoelectric body sometimes occurs when polarization treatment is performed again. Thus, according to the technique described in Japanese Patent No. 4609902, there are restrictions on the method for producing the composite piezoelectric body, and this produces a problem that production cost is increased. Additionally, the surface roughness of the ceramic material is increased by the plasma etching processing, and as a result, when the composite piezoelectric body is adhered to other members such as a reflection matching layer and an acoustic matching layer with adhesive agent, a thickness of an adhesion layer arising from this adhesive agent is increased, and sometimes it exerts influence on transmission/reception of ultrasound.

The present invention is made in view of the foregoing circumstances, and objects of the present invention are to provide a method for producing a composite piezoelectric body, a method for producing ultrasound probe, a composite piezoelectric body, an ultrasound probe and an ultrasound diagnostic imaging apparatus, by which a polarization structure of piezoelectric material such as ceramic is prevented from deteriorating, highly reliable electrodes can be formed at low cost, and the surface roughness of the composite piezoelectric body can be reduced, etc.

In order to achieve at least one of the above objects, a method for producing a composite piezoelectric body, to which one aspect of the present invention is reflected, includes: forming a composite piezoelectric body by filling a non-conductive polymer between a plurality of piezoelectric materials arranged in an array state at predetermined intervals, and polishing one surface of the composite piezoelectric body, from which surface at least the piezoelectric materials and the polymer are exposed, by using an abrasive film in which an abrasive particle is applied to a base film.

Preferably, in the above method for producing the composite piezoelectric body, a grain size of the abrasive particle is 3 µm or less.

Moreover, a method for producing an ultrasound probe by using the composite piezoelectric body produced by the above method for producing the composite piezoelectric body includes: forming the ultrasound probe by laminating a backing layer, an acoustic reflection layer having a higher acoustic impedance than an acoustic impedance of the composite piezoelectric body, the composite piezoelectric body and an acoustic matching layer in this order, and adhering the backing layer, the acoustic reflection layer, the composite piezoelectric body and the acoustic matching layer to one another with an adhesive agent, and the polishing step polishes a surface of the composite piezoelectric body, which surface is adhered to the acoustic reflection layer, by using the abrasive film.

Furthermore, in order to achieve at least one of the above objects, a composite piezoelectric body to which one aspect of the present invention is reflected includes: a plurality of piezoelectric materials each having a column shape arranged in an array state at predetermined intervals; and a non-conductive polymer located between the piezoelectric materials, and a surface roughness of each of the piezoelectric materials and the polymer on one surface of the composite piezoelectric body, from which surface at least the piezoelectric materials and the polymer are exposed, is 0.2 μm or less.

Moreover, in order to achieve at least one of the above objects, an ultrasound probe to which one aspect of the present invention is reflected includes: a backing layer; the composite piezoelectric body of claim 4; and an acoustic matching layer, and the ultrasound probe is constituted by laminating the backing layer, the composite piezoelectric body and the acoustic matching layer in this order.

Preferably, in the above ultrasound probe, an acoustic reflection layer having a higher acoustic impedance than an acoustic impedance of the composite piezoelectric body is laminated between the backing layer and the composite piezoelectric body, and a surface roughness of each of the piezoelectric materials and the polymer on a surface of the composite piezoelectric body, which surface is adhered to at least the acoustic reflection layer, is 0.2 μm or less.

Furthermore, an ultrasound diagnostic imaging apparatus, to which one aspect of the present invention is reflected, includes: the ultrasound probe of claim 5; a transmission section which transmits, to the ultrasound probe, a transmitting signal for applying a voltage to the composite piezoelectric body; a reception section which receives an electronic signal converted by the ultrasound probe as a received signal; an image processing section which generates ultrasound image data on the basis of the received signal received by the reception section; and a display section which displays an ultrasound image based on the ultrasound image data generated by the image processing section.

BRIEF DESCRIPTION OF THE DRAWINGS

The present invention will become more fully understood from the detailed description given hereinbelow and the appended drawings, and thus are not intended as a definition of the limits of the present invention, and wherein.

PREFERRED EMBODIMENT OF THE PRESENT INVENTION

Hereinafter, an embodiment of the present invention will be described with reference to the drawings. In this regard, however, the scope of the present invention is not limited to illustrated examples. Incidentally, the same symbols are used for the same functions and configurations and descriptions thereof are omitted in the following description.

Figure 1:
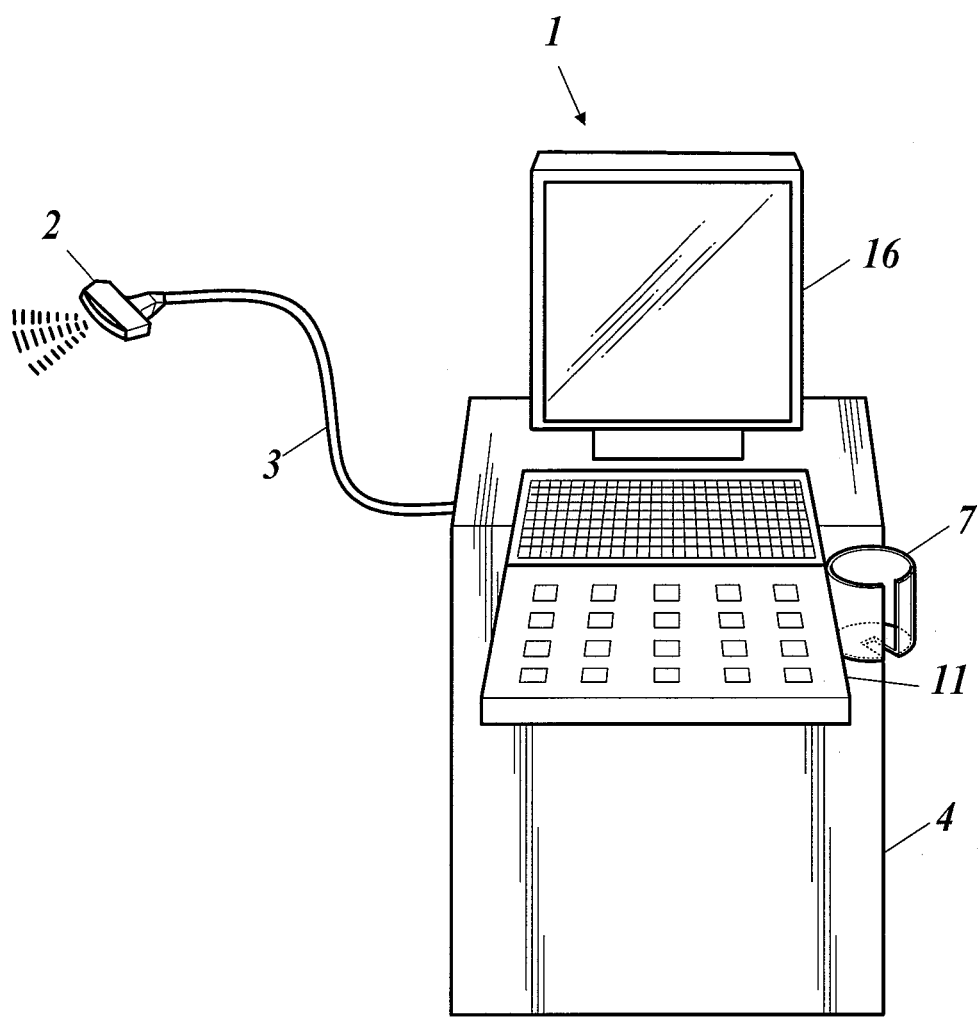
FIG. 1 is a perspective view illustrating an exterior appearance of an ultrasound diagnostic imaging apparatus according to this embodiment.

As illustrated in FIG. 1, an ultrasound diagnostic imaging apparatus 1 according to this embodiment includes an ultrasound probe 2 and a diagnosis apparatus main body 4, which are connected to each other via a cable 3. The ultrasound probe 2 transmits ultrasound (transmitting ultrasound) to a non-illustrated test object such as a biological body, and receives ultrasound (reflected ultrasound) reflected on the test object. In this embodiment, the ultrasound probe 2 is constructed by arranging a plurality of ultrasound transducers 21 (see FIG. 2) in an array state. The diagnosis apparatus main body 4 transmits a transmitting signal of an electrical signal via the cable 3 to cause the ultrasound probe 2 to transmit ultrasound, and images an internal state of the test object as a tomographic image on the basis of a received signal converted from the ultrasound received by the ultrasound probe 2.

The diagnosis apparatus main body 4 is equipped with an operation input section 11 and a display section 16 in the superior region thereof. The operation input section 11 includes switches, buttons, a trackball, a mouse, keyboard, etc. for performing various setting operations, and enables a user to input a command to start diagnosis, data such as personal information of the test object, etc. The display section 16 displays an image for supporting operations with the operation input section 11, ultrasound images created on the basis of the received signal, etc. In addition, a holder 7 which holds the ultrasound probe 2 during nonuse is provided in proper place in the operation input section 11 and/or the diagnosis apparatus main body 4.

Figure 2:
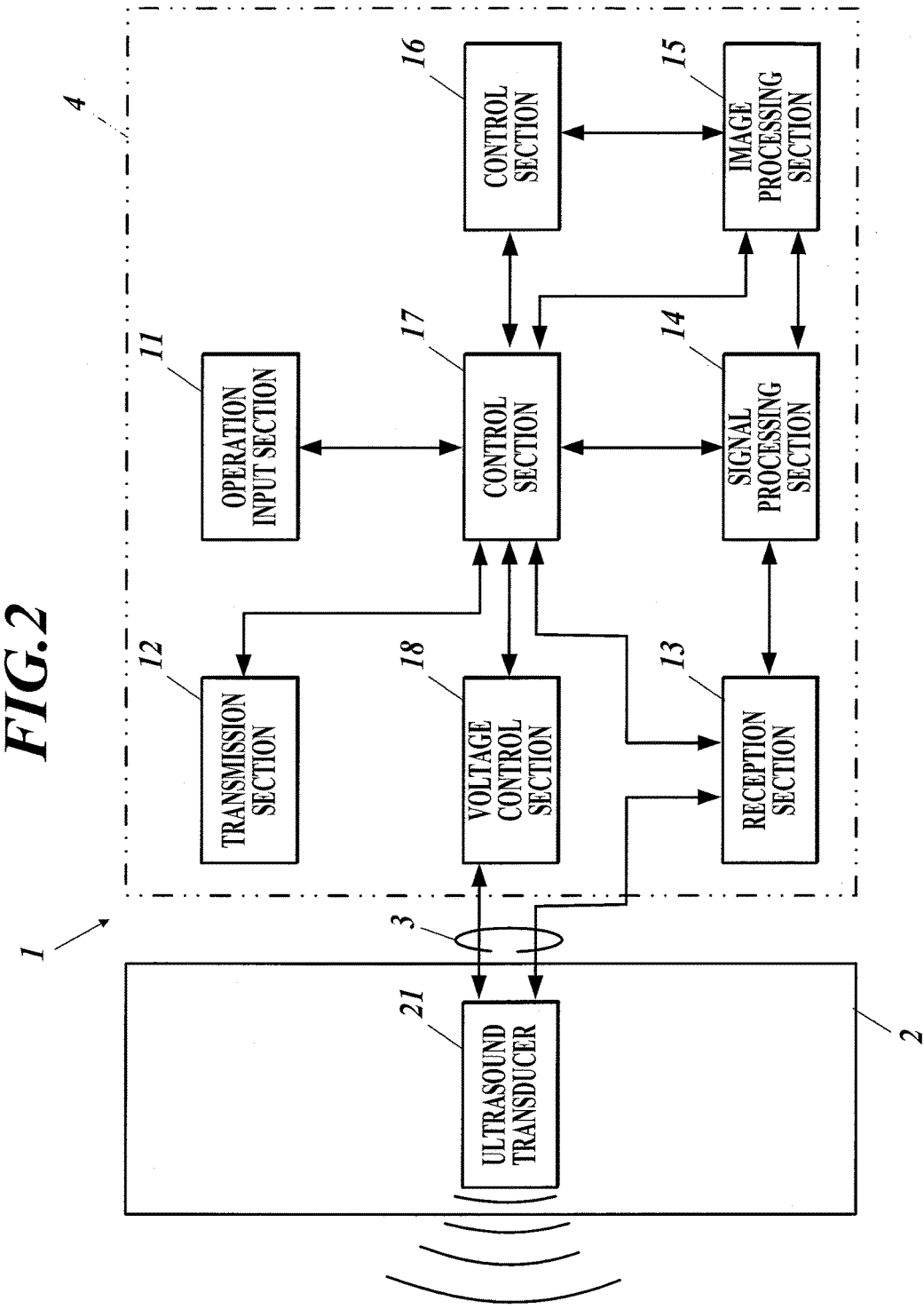
FIG. 2 is a block diagram illustrating a functional configuration of a diagnosis apparatus main body.

Next, the functional configuration of the diagnosis apparatus main body 4 will be described with reference to FIG. 2. The diagnosis apparatus main body 4 is equipped with, in addition to the above-described operation input section 11 and the display section 16, for example, a transmission section 12, a reception section 13, a signal processing section 14, an image processing section 15, a control section 17, and a voltage control section 18.

The transmission section 12 is a circuit which generates a transmission pulse as the transmitting signal to be transmitted to the ultrasound probe 2. The transmission section 12 outputs the transmission pulse to the voltage control section 18 via the control section 17. The amplitude of the transmission pulse is amplified in the voltage control section 18 and then the transmission pulse is transmitted to the ultrasound probe 2. The ultrasound probe 2 outputs the transmitting ultrasound according to the received transmission pulse. At that time, the transmission section 12 forms the transmission beam so that the transmitting ultrasound from each of the ultrasound transducers 21 converges on a predetermined focus position. Incidentally, the above-described transmitting ultrasound can be composed of a plurality of encoded pulses each of which is stretched in a time axis direction.

The reception section 13 is a circuit which receives a received signal of an electronic signal from the ultrasound probe 2 via the cable according to the control by the control section 17, and outputs the received signal to the signal processing section 14.

The signal processing section 14 detects the reflected ultrasound from the output of the reception section 13.

The image processing section 15 is a circuit which generates image data (ultrasound image data) of an internal state of a test object on the basis of the received signal which has been processed in the signal processing section 14 according to the control by the control section 17.

The display section 16 is a device which displays an ultrasound image of the test object on the basis of the ultrasound image data generated in the image processing section 15. The display section 16 is embodied by a display device such as a Cathode-Ray Tube (CRT) display, a Liquid Crystal Display (LCD), an organic Electronic Luminescence (EL) display, an inorganic EL display and a plasma display, and/or a printing device such as a printer.

The control section 17 is a circuit which is configured to include a microprocessor, a memory element and peripheral circuits thereof, and performs total control of the ultrasound diagnostic imaging apparatus 1 by controlling the operation input section 11, the transmission section 12, the voltage control section 18, the reception section 13, the signal processing section 14, the image processing section 15 and the display section 16 depending on their functions.

Figure 3:
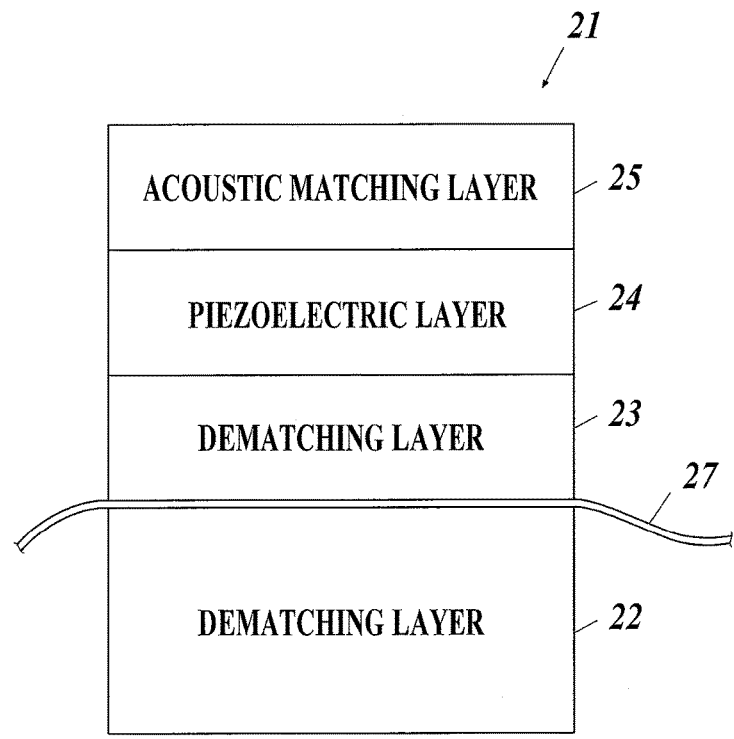
FIG. 3 is a cross-sectional view schematically illustrating a configuration of an ultrasound transducer.

As illustrated in FIG. 3, each of the ultrasound transducers 21 is constructed, for example, by laminating a backing (rear) layer 22, a dematching (acoustic reflection) layer 23, a piezoelectric layer 24 and an acoustic matching layer 25 in order from below at direct light viewing angle on the drawing, and the layers are adhered to one another with adhesive agent such as epoxy type adhesive agent. Incidentally, an acoustic lens may be laminated on the acoustic matching layer 25 as necessary.

The backing layer 22 is an ultrasound absorber which supports the dematching layer 23 and is capable of absorbing unnecessary ultrasound. Concretely, the backing layer 22 is across the piezoelectric layer 24 from the test object, and absorbs ultrasound which is generated from the opposite side of the piezoelectric layer 24 with respect to the side thereof directed toward the test object, and reaches the backing layer 22. Incidentally, in this embodiment, also the configuration without the backing layer 22 may be adopted.

As a backing material constituting the backing layer 22, there are can be used resins including thermoplastics resin such as chloroethylene, polyvinyl butyral (PVB), ABC resin, polyurethane (PUR), polyvinyl alcohol (PVAL), polyethylene (PE), polypropylene (PP), polyacetal (POM), polyethylene terephthalate (PETP), fluorine resin (PTFE), polyethyleneglycol, and polyethylene terephthalate-polyethyleneglycol copolymer; natural rubber; ferrite rubber; epoxy resin; silicone resin; and a composite material obtained by adding a powder such as tungsten oxide, titanium oxide and ferrite to any of the above resins and performing press molding. Also a material obtained by crushing the composite material, then mixing it with the above-described thermoplastics resin and/or epoxy resin, and hardening the mixture may be used. In order to adjust an acoustic impedance, an inorganic material including MACOR® glass and/or porous material including voids may be used.

Preferably, the backing material is composed of a rubber composite and/or epoxy composite, and the form thereof may be arbitrary selected depending on the form of the piezoelectric layer 24 and/or the ultrasound probe 2.

The dematching layer 23 as the acoustic reflection layer is made of a material having a larger acoustic impedance than that of the piezoelectric layer 24. The ultrasound output from the opposite side of the piezoelectric layer 24 with respect to the side thereof directed toward the test object is reflected on the dematching layer 23. As the material applied to the dematching layer 23, any materials such as tungsten and tantalum may be adopted as long as the acoustic impedance difference between the piezoelectric layer 24 and the dematching layer 23 becomes large, and especially tungsten carbide is preferable. Also materials obtained by mixing tungsten carbide with other materials may be adopted. In this embodiment, by providing the dematching layer 23, the sensitivity of the piezoelectric layer 24 with respect to transmitting/received ultrasound can be further improved.

The piezoelectric layer 24 of this embodiment is composed of a composite piezoelectric body in which the piezoelectric bodies and the polymer layers each having a prismatic shape are arranged alternately in one-dimensional array state.

As material of the piezoelectric body, in addition to crystal, piezoelectric ceramics PZT, and PZLT which have been conventionally used, and in addition to an inorganic piezoelectric material such as a thin film of piezoelectric single crystal PZN-PT, PMN-PT, $LiNbO_3$, $LiTaO_3$, $KNbO_3$, ZnO and/or AIN, there can be adopted an organic piezoelectric material such as polyvinylidene fluoride, polyvinylidene fluoride copolymer, polyvinylidene cyanide, vinylidene cyanide copolymer, an odd-numbered nylon such as nylon 9 and nylon 11, aromatic nylon, alicyclic nylon, polylactic acid, polyhydroxy carboxylic acid such as polyhydroxybutyrate, cellulose derivative, polyurea, and so on. Additionally, a composite material obtained by combining the inorganic piezoelectric material with the organic piezoelectric material, or combining the inorganic piezoelectric material with an organic polymeric material can also be adopted.

As the inorganic piezoelectric material among the above-described piezoelectric materials, commercially available one can be used. For example, there can be adopted C-6, C-6H, C-62, C-63, C-64, C-601, C-7, C-8, C-82, C-83H, C-84, C-9, C-91, C-91H, C-92H, C-93 and C-94 which are produced by Fuji Ceramics Corporation, or L-1A, L-6A, L-201F, L-11, L-9, L-155N and L-145N which are produced by Tayca corporation, etc. As the organic piezoelectric material, there can be adopted a PVDF film produced by Tokyo Sensor Co., Ltd., poly(vinylidene fluoride-co-trifluoroethylene) film produced by Kureha Corporation, and poly (vinylidene fluoride-co-hexafluoropropylene) produced by Sigma-Aldrich Co. as a reagent.

As the material of the polymer layer, there can be adopted thermosetting resin such as epoxy resin, phenol resin, urea resin, melanin resin, polyester, polysilicon, polyurethane and silicone resin, and thermoplastics resin such as polyolefin, polyacetal, polycarbonate, polyphenylene sulfide, polyamide, polyimide, polyamide-imide and polyetheretherketone, etc. In addition, also the material obtained by mixing fine particles with the above materials. As the fine particles, there can be adopted the fine particles composed of inorganic material such as ferrite, zinc oxide, silica, glass and carbon, or organic material such as polymer, and as the form thereof, in addition to a spherical form, a slightly crushed form thereof and/or a form having anisotropy may be adopted. Also a hollow-particle form and a complex of more than two kinds of materials may be adopted.

The piezoelectric layer 24 constructed as described above is produced by a known producing method. Concretely, grooves are formed in an array state at predetermined intervals by cutting the piezoelectric material such as a piezoelectric ceramic and a single crystal. It is also possible to cut the piezoelectric material into pieces each having a predetermined size and form a plurality of piezoelectric bodies while leaving spaces of predetermined intervals therebetween. The plurality of piezoelectric bodies may be formed with a mold. Then the polymer layer is formed by filling the spaces between the piezoelectric bodies with the polymer and curing the filled polymer. After that, the upper and lower surfaces of the piezoelectric bodies and the polymer layer, which has been integrated so as to have a predetermined thickness, are ground. Specifically, for example, the integrated piezoelectric bodies and polymer layer is placed on a flat discoid lapping machine, and the lapping machine is caused to slide along the surfaces of the integrated piezoelectric bodies and polymer layer while adding pressures on the upper and lower surfaces thereof, and while pouring liquid polishing agent obtained by mixing loose abrasive with liquid thereinto, so that the upper and lower surfaces are polished. Thus, the composite piezoelectric body is formed. On the upper and lower surfaces of the composite piezoelectric body which has been subjected to grinding, electrodes are attached so that the composite piezoelectric body is put therebetween, and polarization treatment is performed by adding a predetermined polarization voltage.

Incidentally, the acoustic impedance of the piezoelectric layer 24 composed of the composite piezoelectric body is determined on the basis of the volume percentages of the piezoelectric bodies and the polymer layer constituting the piezoelectric layer 24. When defining the acoustic impedance of the piezoelectric bodies as $Z_A$ (MRayls), defining the volume percentage of the piezoelectric bodies as $V_A$ (vol %), defining the acoustic impedance of the polymer layer as $Z_B$ (MRayls), and defining the volume percentage of the polymer layer as $V_B$ (vol %), the acoustic impedance $V_{TOTAL}$ (MRayls) of the piezoelectric layer 24 can be obtained by the following formula (1).

$$V_{TOTAL} = (Z_A \times V_A + Z_B \times V_B)/100 \quad (1)$$

In the meanwhile, the above-described grinding processing is performed while applying the pressure on the upper and lower surfaces of the integrated piezoelectric bodies and polymer layer. Thus, the polymer layer is contracted by the pressure during the grinding, and is ground in the contracted state. Therefore, when releasing the pressure and terminating the grinding processing, the contracted polymer layer is restored, and the polymer layer sometimes bulges more than the piezoelectric bodies so as to form steps. For this reason, in this embodiment, processing to polish the both surfaces of the composite piezoelectric body by using an abrasive film, in which abrasive particles are applied to a base film, is further performed.

Figure 4:
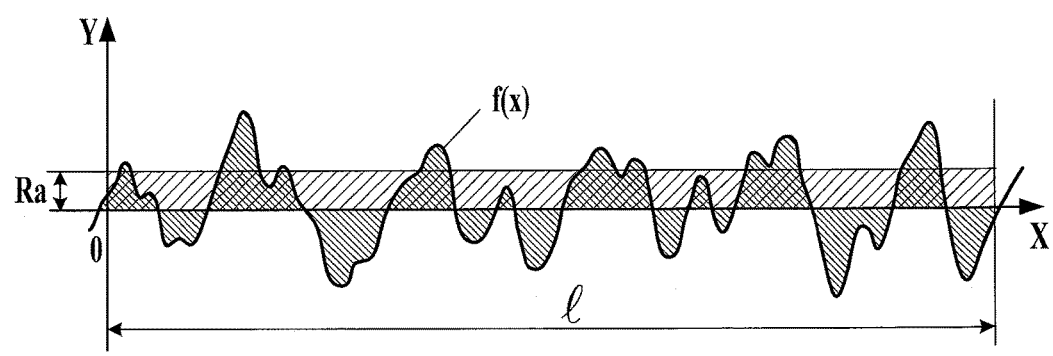
FIG. 4 is a graph for explaining about a roughness curve.

As the base film which can be applied to this embodiment, for example, there can be adopted a film of plastic such as polyimide, polyamide, polyimide-amide, polyethylene terephthalate (PETP), polyester such as polyethylenenaphthalate, polyacrylate such as polymethylmethacrylate (PMMA), polymethacrylate, polycarbonate resin, polyurethane, cycle-olefin polymer, etc. As the material of the abrasive particles which can be applied to this embodiment, there can be adopted inorganic material such as silicon carbide (SiC), aluminum oxide ($Al_2O_3$), chrome oxide ($Cr_2O_3$), iron oxide ($Fe_2O_3$), diamond (C), cerium oxide ($CeO_2$) and silicon oxide ($SiO_2$), organic material such as phenolic resin and epoxy resin, and/or material obtained by compounding the above-described inorganic material and organic material. The grain size of each abrasive particle may be 9 μm or less, and more preferably, 3 μm or less. In this embodiment, the composite piezoelectric body is polished until each of surface roughnesses (Ra) of the piezoelectric bodies and the polymer layer in at least three randomly-selected regions of 0.2 mm×0.2 mm on the both surfaces of the composite piezoelectric body becomes 0.2 μm or less. Although the polishing treatment is performed with respect to the both surfaces of the composite piezoelectric body in this embodiment, the polishing treatment may be performed only to one surface (surface facing the dematching layer 23). Here, the surface roughness (Ra) means an arithmetic average roughness. To obtain the arithmetic average roughness, for example as illustrated in FIG. 4, the surface roughness is measured at plural points by a measuring device such as a confocal laser scanning microscope to obtain a roughness curve. The method for measuring the surface roughness may be either of contact type or non-contact type. Then, when extracting a portion of a reference length (l) in a direction along an average line from the roughness curve and representing the roughness curve by "y=f(x)" with the average line direction of the extracted portion as X axis and a longitudinal magnification direction as Y axis, the surface roughness (Ra) is the value obtained by the following formula (2) and represented by micrometer (μm). This is the surface roughness in one-dimensional line, but the surface roughness (Ra) of the present invention includes also the surface roughness obtained by expanding this way of thinking in two-dimensional plane.

[Formula 1]

$$Ra = \frac{1}{l} \int_0^l |f(x)| dx \quad (2)$$

According to this embodiment, the exposed portions of the piezoelectric bodies and the polymer layer of the composite piezoelectric body can be polished simultaneously, and furthermore, the composite piezoelectric body which has been subjected to the polarization treatment is not depolarized. Also bulging portions of the polymer layer can be polished appropriately. Therefore, highly reliable electrodes can be formed at low cost, and it becomes possible to form the composite piezoelectric body having the surface roughness similar to that of a mirror surface.

Figure 5:
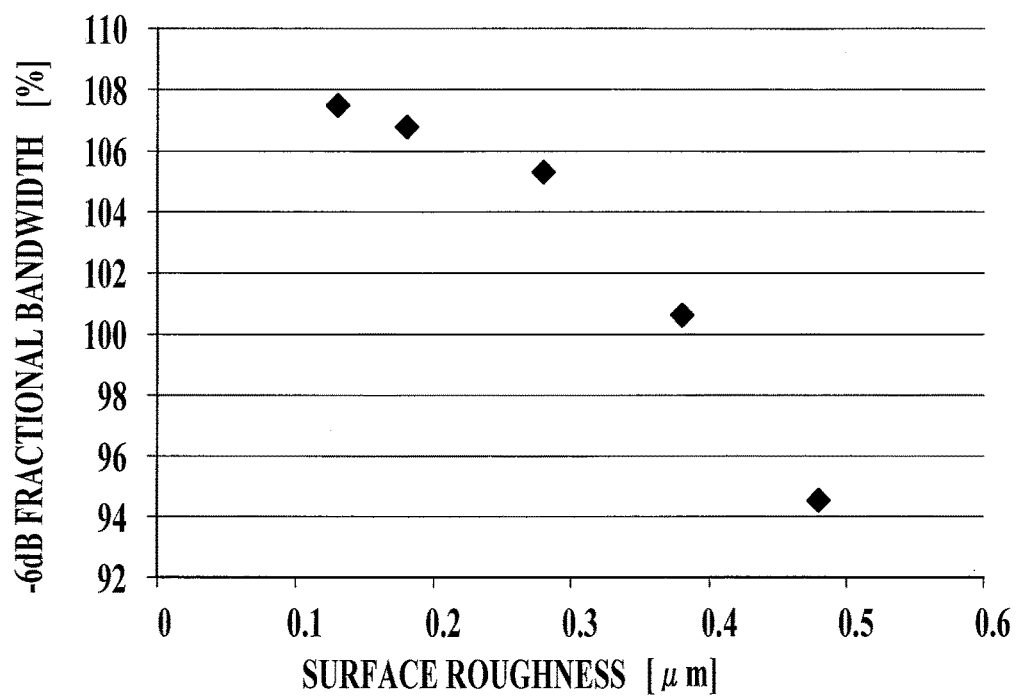
FIG. 5 is a graph illustrating a relationship between a surface roughness of a composite piezoelectric body and a bandwidth of the ultrasound transducer.

Here, the relationship between the surface roughness of the composite piezoelectric body and the bandwidth of the ultrasound probe 2 will be described. The layer thickness of the adhesion layer, which is formed by the adhesive agent used for adhering the piezoelectric layer 24 and the dematching layer 23 to each other, depends on the surface roughness of the composite piezoelectric body of the piezoelectric layer 24, and the larger the surface roughness is, the larger the layer thickness of the adhesion layer becomes. The larger the layer thickness of the adhesion layer becomes, the lower the high-frequency-side sensitivity becomes and the narrower the bandwidth of the ultrasound probe 2 becomes. Thus, the smaller the surface roughness is, the easier the ultrasound probe 2 maintains a broad bandwidth. Here, the relationship between the surface roughness of the composite piezoelectric body and a fractional bandwidth at −6 dB of the ultrasound probe 2 is illustrated in FIG. 5. Incidentally, the surface roughness of the dematching layer 23 is set to 0.15 μm. As illustrated in FIG. 5, when the surface roughness of the composite piezoelectric body becomes 0.3 μm or more, −6 dB fractional bandwidth drops drastically. Thus, it seems preferable to set the surface roughness of the composite piezoelectric body to 0.3 μm or less according to FIG. 5, but when the surface roughness of the composite piezoelectric body is 0.2 μm or more, −6 dB fractional bandwidth varies significantly due to production variation. For this reason, in this embodiment, the composite piezoelectric body is polished until the surface roughness thereof becomes 0.2 μm or less.

Thus, because the surface roughness of the composite piezoelectric body is 0.2 μm or less in this embodiment, the layer thickness of the adhesion layer can be small, therefore the adhesion layer can be suitably used in the ultrasound probe for high-frequency applications or the ultrasound probe using the dematching layer 23, and thereby high sensitivity can be maintained.

The electrodes are formed on the composite piezoelectric body produced as described above by firstly forming base metal such as titanium (Ti) and chrome (Cr) by a sputtering method so that the thickness thereof is in the range of 0.02 to 1.0 μm, then partially mixing insulating material with metal material composed mainly of metal element, or with metal material composed of alloy thereof, as necessary, and forming the mixture so as to have a thickness in the range of 1 to 10 μm by an appropriate method such as a sputtering method. As the metal material, there are used gold (Au), platinum (Pt), silver (Ag), palladium (Pd), copper (Cu), nickel (Ni), stannum (Sn), etc. The electrodes can be formed also by applying conductive paste obtained by mixing fine metal powder with low-melting-point glass by screen printing, dipping method, thermal spraying method, or the like, in addition to the above-described sputtering method.

The backing layer 22 and the dematching layer 23 holds Flexible Printed Circuits (FPC) 27 therebetween, and the transmitting signal from the voltage control section 18 is applied to the piezoelectric layer 24 by the FPC 27. The received signal generated in the piezoelectric layer 24 is applied to the reception section 13 by the FPC 27.

The acoustic matching layer 25 performs acoustic impedance matching between the piezoelectric layer 24 and the test object, and thereby suppresses reflection on a boundary plane. The acoustic matching layer 25 is placed on the side of the piezoelectric layer 24 directed toward the test object, through which side the ultrasound is transmitted/received. The acoustic matching layer 25 has the acoustic impedance which is approximately intermediate between those of the piezoelectric layer 24 and the test object.

As the material used for the acoustic matching layer 25, there can be adopted aluminum, aluminum alloy (for example, AL-Mg alloy), magnesium alloy, MACOR® glass, glass, fused quartz, copper graphite, polyethylene (PE), polypropylene (PP), polycarbonate (PC), ABC resin, ABS resin, AAS resin, AES resin, nylon (PA6, PA6-6), polyphenyleneoxide (PPO), polyphenylene sulfide (PPS: also glass fiber filled is good), polyphenylenether (PPE), polyetheretherketone (PEEK), polyamide-imide (PAI), polyethylene terephthalate (PETP), epoxy resin, urethane resin, etc., and a composite material obtained by mixing the above material with other materials. Preferably, the material obtained by adding, as filler, zinc oxide, titanium oxide, silica, alumina, red iron oxide, ferrite, tungsten oxide, ytterbium oxide, barium sulfate, tungsten, molybdenum, organic fine particles, etc. to thermosetting resin such as epoxy resins is adopted.

The acoustic matching layer 25 may be composed of a single layer or multiple layers, but preferably, it is composed of two or more layers, and more preferably, four or more layers. The layer thickness of the acoustic matching layer 25 is preferably set so as to be λ/4 when defining a wavelength of ultrasound transmitting through the matching layer as λ. The thickness of such acoustic matching layer depends on a central frequency, but generally the matching layer of thickness in the range of approximately 20 to 500 μm is used. The acoustic matching layer 25 is formed by adhesive lamination or multilayer application in a thickness direction, and acoustic impedance matching is performed by making the respective layers have different material compositions from one another and performing weighing of the acoustic impedances in the thickness direction. Incidentally, the direction of the acoustic impedance weighing in the acoustic matching layer 25 is not limited to the thickness direction, and may be a horizontal direction.

Example 1

Hereinafter, the present invention will be described in more detail by examples, but it is a matter of course that the present invention is not limited to these examples.
<Production of Composite Piezoelectric Body>
In a general-purpose ceramic piezoelectric material (10 mm×60 mm×1 mm), grooves each having a width of 15 μm and a depth of 0.4 mm were formed continuously at intervals of 80 μm along a long side, and then the ceramic piezoelectric material was washed. The shaped grooves were filled with epoxy resin, and the filled epoxy resin was completely cured by gradually increasing a temperature from room temperature. After that, the upper and lower surfaces of the ceramic piezoelectric material, in which the epoxy resin was added, were ground so that the ceramic electronic material and the epoxy resin were exposed from the both surfaces, and the upper and lower surfaces of the composite piezoelectric material were further ground until the thickness thereof became 125 μm. Then the upper and lower surfaces of the composite piezoelectric material were further polished by using the abrasive film, in which artificial diamond abrasive particles each having a grain size of 3 μm were applied on the base film, so that the thickness of the composite piezoelectric material became 120 μm. After that, the composite piezoelectric material was cut into pieces each having a size of 4.6 mm×42.5 mm, and the electrodes were formed and polarization treatment was performed, and thereby composite piezoelectric bodies 1-1 to 1-3 were produced. Additionally, composite piezoelectric bodies 2-1 to 2-3 each having a thickness of 80 μm were produced by the same producing method. Moreover, as comparative examples, by omitting the polishing step with the abrasive film, comparative composite piezoelectric bodies 1-1 and 1-2 each having a thickness of 120 μm, and comparative composite piezoelectric body having a thickness of 80 μm were produced. The roughnesses (Ra) of the composite piezoelectric bodies are set as illustrated in following Table 1.
<Production of Ultrasound Probe>
Firstly, the acoustic matching layer was produced by laminating four layers of acoustic matching materials. The acoustic matching material of each layer was produced with the use of kneaded and cured material of epoxy resin and ferrite or silicon resin fine powder so as to meet the following conditions. Concretely, the acoustic impedance was set to 2.0 MRayls and the thickness was set to 40 μm with respect to the acoustic matching material of the uppermost layer, which is the acoustic-emitting-surface-side outermost layer, the acoustic impedance was set to 4.0 MRayls and the thickness was set to 40 μm with respect to the acoustic matching material of the second layer, the acoustic impedance was set to 6.0 MRayls and the thickness was set to 50 μm with respect to the acoustic matching material of the third layer, and the acoustic impedance was set to 11.0 MRayls and the thickness was set to 60 μm with respect to the acoustic matching material of the fourth layer (undermost layer). The acoustic matching materials of the layers produced in this way were laminated in the above-described order and adhered to one another with epoxy adhesive agent by thermal curing under the pressurized condition of 2.94 MPa, and then formed to have a size of 4.6 mm×42.5 mm so as to be the acoustic matching layer.

Next, by using the composite piezoelectric body 1-1 produced as described above, the piezoelectric layer was produced by forming insulating grooves along a longitudinal direction in the vicinity of both ends of a short axis on a rear side of the composite piezoelectric body 1-1 so that an effective aperture in a short axis direction becomes 4.0 mm, and then forming a signal electrode and a ground electrode.

After that, on the object obtained by laminating and adhering the patterned FPC, the backing layer and a fixation plate to one another in the adhesion conditions same as above, the piezoelectric layer and the acoustic matching layer produced as described above were laminated in order, and adhered to each other. Incidentally, the acoustic matching layer was adhered so that the acoustic matching material having a high acoustic impedance was made contact with the piezoelectric layer. Then, with respect to the laminated body produced in this way, dicing was performed so that the piezoelectric layer was completely divided at intervals of 0.2 mm in a longitudinal direction (azimuth direction) by using a blade having a thickness of 20 μm and thereby elements were made, and further dicing was performed to the divided elements so that the acoustic matching layer was completely divided at intervals of about 67 μm by using the above blade and thereby a transducer was produced.

After that, the insulating layer of about 3 μm made of polyparaxylene was formed on the surface of the transducer, and the acoustic lens was laminated and adhered on the acoustic emitting surface of the insulating layer so that a vibration portion was produced.

Next, after connecting a connector to the FPC, the vibration portion produced as described above was housed in a case so that the ultrasound probe of Example 1-1 was produced.

Subsequently, by using each of composite piezoelectric bodies 1-2 to 1-3 and comparative composite piezoelectric bodies 1-1 to 1-2 instead of composite piezoelectric body 1-1, with other materials and producing process same as above, the ultrasound probes of Examples 1-2 to 1-3 and Comparative example 1-1 to 1-2 were produced.

Example 2

Next, as Example 2, the ultrasound probe was produced as described below.

Firstly, the acoustic matching layer was produced by laminating six layers of acoustic matching materials. The acoustic matching material of each layer was produced with the use of kneaded and cured material of epoxy resin and ferrite or silicon resin fine powder so as to meet the following conditions. Concretely, the acoustic impedance was set to 1.5 MRayls and the thickness was set to 20 μm with respect to the acoustic matching material of the uppermost layer, which is the acoustic-emitting-surface-side outermost layer, the acoustic impedance was set to 2.0 MRayls and the thickness was set to 30 μm with respect to the acoustic matching material of the second layer, the acoustic impedance was set to 3.0 MRayls and the thickness was set to 30 μm with respect to the acoustic matching material of the third layer, the acoustic impedance was set to 6.0 MRayls and the thickness was set to 40 μm with respect to the acoustic matching material of the fourth layer, the acoustic impedance was set to 9.0 MRayls and the thickness was set to 50 μm with respect to the acoustic matching material of the fifth layer, and the acoustic impedance was set to 14.0 MRayls and the thickness was set to 60 μm with respect to the acoustic matching material of the undermost layer. The acoustic matching materials of the layers produced in this way were laminated in the above-described order and adhered to one another with epoxy adhesive agent by thermal curing under the pressurized condition of 2.94 MPa, and then formed to have a size of 4.6 mm×42.5 mm so as to be the acoustic matching layer.

Next, by using the composite piezoelectric body 2-1 produced as described above, the piezoelectric layer was produced by forming insulating grooves along a longitudinal direction in the vicinity of both ends of a short axis on a rear side of the composite piezoelectric body 2-1 so that an effective aperture in a short axis direction becomes 4.0 mm, and then forming a signal electrode and a ground electrode.

Then, tungsten carbide was formed so as to have a size of 4.6 mm×42.5 mm×80 μm so as to become the dematching layer. The piezoelectric layer and the dematching layer produced as described above were then laminated and adhered to each other, and then dicing was performed to form grooves each having a width of 40 μm and a depth of 90 μm in the dematching layer from the rear surface thereof along a longitudinal direction so that the grooves communicate with the insulating groove formed in the piezoelectric layer. Thus, a vibration layer was obtained.

After that, on the object obtained by laminating and adhering the patterned FPC, the backing layer and the fixation plate to one another in the adhesion conditions same as above, the vibration layer and the acoustic matching layer produced as described above were laminated in order, and adhered to each other. By this, the signal electrode and the ground electrode of the piezoelectric layer are connected to a signal electrode surface and a ground electrode surface formed on the FPC with the dematching layer as a wiring, respectively, while maintaining an insulating state of these electrodes. Incidentally, the acoustic matching layer was adhered so that the acoustic matching material having a high acoustic impedance was made contact with the piezoelectric layer. Then, with respect to the laminated body produced in this way, dicing was performed so that the vibration layer was completely divided at intervals of 0.2 mm in a longitudinal direction (azimuth direction) by using a blade having a thickness of 20 μm so that elements were made, and further dicing was performed to the divided elements so that the acoustic matching layer was completely divided at intervals of about 67 μm by using the above blade so that transducer was produced.

After that, the insulating layer of about 3 μm made of polyparaxylene was formed on the surface of the transducer, and the acoustic lens was laminated and adhered on the acoustic emitting surface of the insulating layer so that the vibration portion was produced.

Next, after connecting the connector to the FPC, the vibration portion produced as described above was housed in the case so that the ultrasound probe of Example 2-1 was produced.

Subsequently, by using each of composite piezoelectric bodies 2-2 to 2-3 and comparative composite piezoelectric body 2-1 instead of composite piezoelectric body 2-1, with other materials and producing process same as above, the ultrasound probes of Examples 2-2 to 2-3 and Comparative example 2-1 were produced.

(Evaluation)

The thickness of the adhesion layer between the piezoelectric layer and the dematching layer or between the piezoelectric layer and the FPC, transmission/reception sensitivity (maximum sensitivity), lower limit frequency (FL6) and upper limit frequency (FH6) and center frequency (FC6) at −6 dB from the maximum sensitivity, −6 dB fractional bandwidth, and robustness of each of the ultrasound probes of Examples 1-1 to 1-3, Examples 2-1 to 2-3, Comparative examples 1-1 to 1-2 and Comparative example 2-1 produced as described above were evaluated in the following conditions. The measuring system was constructed by a general-purpose function generator (produced by Agilent Technologies, Inc.; 33220A) a power amplifier (produced by Hewlett-Packard, Co.; 8447D) and an oscilloscope (produced by Textronix, Inc.; TPS5032), and a reflective plate composed of SUS was located in a degassed water. The ultrasound probe was fixed in a position where the focal distance of the ultrasound probe and the distance from the ultrasound probe to the reflective plate matched each other and the transmission/reception sensitivity of the ultrasound probe became highest. Then signal transmission was performed by burst-wave driving at Vpp 80 [V], and comparison of transmission/reception sensitivities was conducted. The surface roughness (Ra) was obtained by obtaining the roughness curve by measurement with the confocal laser scanning microscope (Olympus Corporation; OLS3000), and calculating the arithmetic average roughness from the roughness curve. The results are illustrated in Table 1. Incidentally, all of the used piezoelectric materials in the following Table 1 were materials produced by Fuji Ceramics Corporation.

TABLE 1

| ULTRASOUND PROBE | COMPOSITE PIEZOELECTRIC BODY | SURFACE ROUGHNESS (Ra) [μm] | THICKNESS OF ADHESION LAYER [μm] | TRANSMISSION/ RECEPTION SENSITIVITY [dB] | −6 dB LOWER LIMIT FREQUENCY (FL6) [MHz] |
|---|---|---|---|---|---|
| EXAMPLE 1-1 | 1-1 | 0.08 | 0.62 | −44.1 | 6.5 |
| EXAMPLE 1-2 | 1-2 | 0.11 | 0.65 | −43.8 | 6.6 |
| EXAMPLE 1-3 | 1-3 | 0.20 | 0.68 | −44.0 | 6.5 |
| COMPARATIVE EXAMPLE 1-1 | COMPARATIVE 1-1 | 0.25 | 0.78 | −44.4 | 6.6 |
| COMPARATIVE EXAMPLE 1-2 | COMPARATIVE 1-2 | 0.30 | 0.83 | −44.7 | 6.5 |
| EXAMPLE 2-1 | 2-1 | 0.09 | 0.28 | −39.2 | 5.1 |
| EXAMPLE 2-2 | 2-2 | 0.13 | 0.31 | −39.2 | 5.2 |
| EXAMPLE 2-3 | 2-3 | 0.19 | 0.36 | −39.5 | 5.1 |
| COMPARATIVE EXAMPLE 2-1 | COMPARATIVE 2-1 | 0.26 | 0.44 | −40.0 | 5.1 |

| ULTRASOUND PROBE | −6 dB UPPER LIMIT FREQUENCY (FH6) [MHz] | −6 dB CENTER FREQUENCY (FC6) [MHz] | −6 dB FRACTIONAL BANDWIDTH [%] | ROBUSTNESS |
|---|---|---|---|---|
| EXAMPLE 1-1 | 16.5 | 11.5 | 87.0 | A |
| EXAMPLE 1-2 | 16.4 | 11.5 | 85.2 | A |
| EXAMPLE 1-3 | 16.0 | 11.3 | 84.4 | A |
| COMPARATIVE EXAMPLE 1-1 | 15.5 | 11.1 | 8.5 | B |
| COMPARATIVE EXAMPLE 1-2 | 14.5 | 10.5 | 76.2 | B |
| EXAMPLE 2-1 | 16.5 | 10.8 | 105.6 | A |
| EXAMPLE 2-2 | 16.4 | 10.8 | 103.7 | A |
| EXAMPLE 2-3 | 16.0 | 10.6 | 103.3 | A |
| COMPARATIVE EXAMPLE 2-1 | 15.5 | 10.3 | 101.0 | B |

RESULTS

Thus, it was found that the layer thickness of the adhesive agent can be reduced, and the ultrasound probe having a broad bandwidth and a good robustness (A) can be obtained, by making the surface roughness (Ra) of the composite piezoelectric body 2.0 μm or less. In the meantime, it was also found that when the surface roughness (Ra) of the composite piezoelectric body exceeded 2.0 μm, a bandwidth of high frequency portion became narrower, and the ultrasound probe having a narrow bandwidth and a poor robustness (B) was obtained.

As described above, according to this embodiment, in the step of forming the composite piezoelectric body, the composite piezoelectric body is formed by filling the spaces between the plural piezoelectric materials arranged in an array state at predetermined intervals with non-conductive polymer. In the polishing step, one surface of the composite piezoelectric body, from which at least the piezoelectric materials and the polymer are exposed, is polished by using the abrasive film obtained by applying abrasive particles to the base film. Because the composite piezoelectric body can be polished while reducing influences of thermal and electrical effects as a result, the polarization structure of the piezoelectric material such as ceramic can be prevented from deteriorating. Therefore, it becomes unnecessary to perform polarization treatment again, and thereby production costs can be reduced. Moreover, because expansion of the polymer is suppressed and steps between the piezoelectric materials and the polymer can be small, highly reliable electrodes can be formed at low costs. Furthermore, the surface roughness of the composite piezoelectric body can be reduced, and thereby the thickness of the adhesion layer arising from the adhesive agent can be reduced when adhering the composite piezoelectric body to other members with the adhesive agent.

Moreover, according to this embodiment, because the grain size of the abrasive particle is set to 3 µm or less, the surface roughness of the composite piezoelectric body can be reduced.

Furthermore, according to this embodiment, in the step of forming the ultrasound probe, the backing layer, the dematching layer having the higher acoustic impedance than the acoustic impedance of the composite piezoelectric body, the composite piezoelectric body and the acoustic matching layer are laminated in this order and adhered to one another to form the ultrasound probe. In the polishing step, at least the surface of the composite piezoelectric body to be adhered to the dematching layer is polished by using the abrasive film. As a result, the layer thickness of the adhesion layer formed between the composite piezoelectric body and the dematching layer can be reduced, high sensitivity can be maintained, and it becomes possible to suitably utilize the ultrasound probe for high-frequency applications and/or the ultrasound probe using the acoustic reflection layer.

Additionally, according to this embodiment, because the surface roughnesses of the piezoelectric materials and the polymer on one surface of the composite piezoelectric body, from which the piezoelectric material and the polymer are exposed, is 0.2 µm or less, highly reliable electrodes can be formed at low costs. It is also possible to reduce the thickness of the adhesion layer arising from the adhesive agent used for adhering the composite piezoelectric body to other materials because the surface roughness of the composite piezoelectric body can be reduced.

Moreover, according to this embodiment, the high sensitivity ultrasound probe can be obtained by constructing it by laminating the backing layer 22, the composite piezoelectric body and the acoustic matching layer 25 in this order.

Furthermore, according to this embodiment, because of laminating the dematching layer 23 having the higher acoustic impedance than the acoustic impedance of the composite piezoelectric body between the backing layer 22 and the composite piezoelectric body, the ultrasound probe having a further higher sensitivity can be obtained.

Incidentally, the descriptions of the embodiment of the present application is a mere example of the ultrasound diagnostic imaging apparatus according to the present invention, and the present invention is not limited thereto. The detailed configurations and operations of the functional sections constituting the ultrasound diagnostic imaging apparatus can be arbitrary changed.

The present U.S. patent application claims a priority under the Paris Convention of Japanese patent application No. 2013-042468 filed on Mar. 5, 2013, in which all contents of this application are disclosed, and which shall be a basis of correction of an incorrect translation.

What is claimed is:

1. A composite piezoelectric body comprising:
   a plurality of piezoelectric materials each having a column shape arranged in an array state at predetermined intervals; and
   a non-conductive polymer located between the piezoelectric materials, wherein a surface roughness of a surface of the composite piezoelectric body, from which surface at least the piezoelectric materials and the polymer are exposed, said surface including surfaces of the piezoelectric materials and the polymer, is in a range of 0.08 µm to 0.2 µm.

2. An ultrasound probe comprising:
   a backing layer;
   the composite piezoelectric body of claim 1; and
   an acoustic matching layer,
   wherein the ultrasound probe is constituted by laminating the backing layer, the composite piezoelectric body and the acoustic matching layer in this order.

3. The ultrasound probe of claim 2, wherein:
   an acoustic reflection layer having a higher acoustic impedance than an acoustic impedance of the composite piezoelectric body is laminated between the backing layer and the composite piezoelectric body, and
   said surface of the composite piezoelectric body is adhered to the acoustic reflection layer.

4. An ultrasound diagnostic imaging apparatus comprising:
   the ultrasound probe of claim 2;
   a transmission section which transmits, to the ultrasound probe, a transmitting signal for applying a voltage to the composite piezoelectric body;
   a reception section which receives an electronic signal converted by the ultrasound probe as a received signal;
   an image processing section which generates ultrasound image data on the basis of the received signal received by the reception section; and
   a display section which displays an ultrasound image based on the ultrasound image data generated by the image processing section.

5. The composite piezoelectric body of claim 1, further comprising:
   an adhesion layer disposed on said surface of the composite piezoelectric body.

* * * * *